United States Patent
Ishizuka et al.

(10) Patent No.: US 7,049,067 B2
(45) Date of Patent: May 23, 2006

(54) OLIGONUCLEOTIDE FOR DETECTION OF HIV-1 AND DETECTION METHOD

(75) Inventors: Tetsuya Ishizuka, Yokohama (JP);
Takahiko Ishiguro, Yokohama (JP);
Juichi Saitoh, Yamato (JP)

(73) Assignee: Tosoh Corporation, Tokyo (JP)

( * ) Notice: Subject to any disclaimer, the term of this patent is extended or adjusted under 35 U.S.C. 154(b) by 2 days.

(21) Appl. No.: 09/984,637

(22) Filed: Oct. 30, 2001

(65) Prior Publication Data

US 2004/0048246 A1   Mar. 11, 2004

(30) Foreign Application Priority Data

Oct. 30, 2000   (JP)   ............................. 2000-334937

(51) Int. Cl.
*C12Q 1/68*   (2006.01)
(52) U.S. Cl. ........................... 435/6; 424/208.1; 435/5; 435/91.2; 435/91.21; 536/24.3
(58) Field of Classification Search ............. 424/208.1; 435/5, 6, 91.2, 91.21, 172.3, 235.1; 536/23.1, 536/24.1, 24.3, 24.33
See application file for complete search history.

(56) References Cited

OTHER PUBLICATIONS

README.txt file from CD-ROM of Professor Andrew Chin.
SHORT.txt file pp. 1-2 of CD-ROM of Professor Andrew Chin.
http://newport.lib.unc.edu/web2/tramp2.exe/authority_hits/A2oicjn4.001?server=3home&item=1.
McDonough, S.H. et al., (1998) "High Throughput Analysis for the Simultaneous or Separate Detection of Human Immunodeficiency Virus (HIV) and Hepatitis Type C Virus (HCV)" Infusionstherapie und Trasnfusionmedizin 25: 164-169.
Muesing, M.A. et al. (1999) "Human Immunodeficiency Virus Type 1, isolate PV22, complete Genome (H9 / HTLV III Proviral DNA)" NCBI PubMed Accession No. K02083.
Muesing, M.A. et al. (1985) "Human Immunodeficiency Virus Type 1, isolate PV22, complete Genome (H9 / HTLV III Proviral DNA)" Nature 313: 450-458.
Romano, J.W. et al. (1995) "Detection of HIV-1 Infection in vitro Using NASBA: an isothermal RNA amplification technioque," *J. Virol. Meth.* 54:109-119.
Romano, J.W. et al. (1996) "NASBA A Novel, Isothermal Technology for Qualitative and Quantitative HIV-1 RNA Measurements," *Clin. Lab. Meth.* 16: 89-103.
Van Gemen, B. et al. (1995) "The One-Tube Quantitative HIV-1 RNA NASBA: Precision, Accuracy and Application," PCR Methods and Applications 4:S177-S184.
Search Report of the European Patent Office, European Patent Application EP 01 12 5378.

*Primary Examiner*—Ulrike Winkler
(74) *Attorney, Agent, or Firm*—Jeffrey I. Auerbach; Berenato, White & Stavish, LLC

(57) ABSTRACT

An oligonucleotide useful for detection of an RNA derived from HIV-1 consisting of at least 10 consecutive bases in any of SEQ ID NOS:1, 2, 4 to 10 and 13 to 17, which can bind to a specific site of the RNA.

6 Claims, 8 Drawing Sheets

Fig. 3

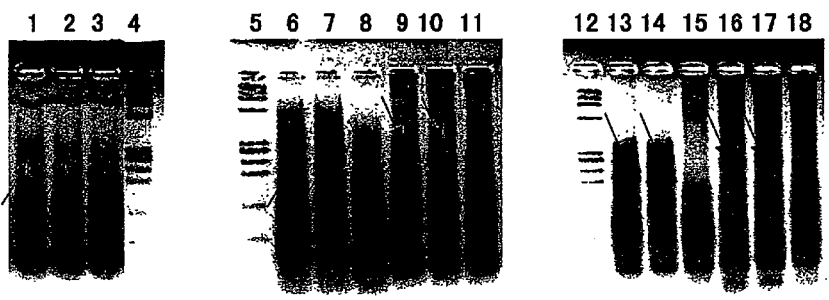

| Lane | First primer | Second primer | Third oligonucleotide | Target RNA |
|---|---|---|---|---|
| 1,2 : | SEQ ID NO: 5 | SEQ ID NO: 19 | SEQ ID NO: 2 | $10^3$ copies |
| 3, : | SEQ ID NO: 5 | SEQ ID NO: 19 | SEQ ID NO: 2 | Nega |
| 6,7 : | SEQ ID NO: 5 | SEQ ID NO: 20 | SEQ ID NO: 3 | $10^3$ copies |
| 8, : | SEQ ID NO: 5 | SEQ ID NO: 20 | SEQ ID NO: 3 | Nega |
| 9,10 : | SEQ ID NO: 6 | SEQ ID NO: 20 | SEQ ID NO: 3 | $10^3$ copies |
| 11, : | SEQ ID NO: 6 | SEQ ID NO: 20 | SEQ ID NO: 3 | Nega |
| 13,14 : | SEQ ID NO: 5 | SEQ ID NO: 21 | SEQ ID NO: 4 | $10^3$ copies |
| 15, : | SEQ ID NO: 5 | SEQ ID NO: 21 | SEQ ID NO: 4 | Nega |
| 16,17 : | SEQ ID NO: 6 | SEQ ID NO: 21 | SEQ ID NO: 4 | $10^3$ copies |
| 18, : | SEQ ID NO: 6 | SEQ ID NO: 21 | SEQ ID NO: 4 | Nega |
| 4,5,12: | DNA molecular weight marker ($\phi$×174/Hae III digest) | | | |

Fig. 4

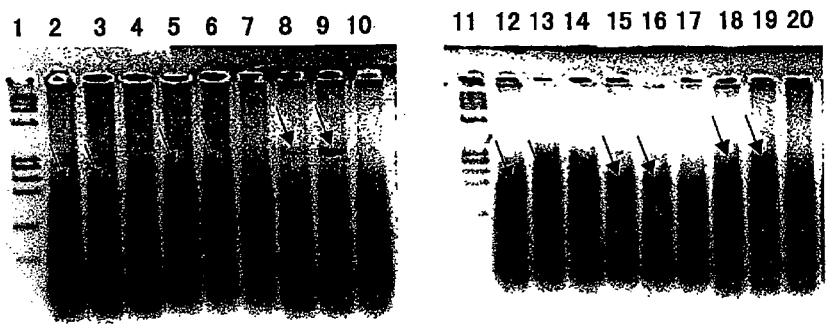

| Lane | First primer | Second primer | Third oligonucleotide | Target RNA |
|---|---|---|---|---|
| 2,3 | SEQ ID NO: 8 | SEQ ID NO: 22 | SEQ ID NO: 5 | $10^3$ copies |
| 4 | SEQ ID NO: 8 | SEQ ID NO: 22 | SEQ ID NO: 5 | Nega |
| 5,6 | SEQ ID NO: 9 | SEQ ID NO: 22 | SEQ ID NO: 5 | $10^3$ copies |
| 7 | SEQ ID NO: 9 | SEQ ID NO: 22 | SEQ ID NO: 5 | Nega |
| 8,9 | SEQ ID NO: 10 | SEQ ID NO: 22 | SEQ ID NO: 5 | $10^3$ copies |
| 10 | SEQ ID NO: 10 | SEQ ID NO: 22 | SEQ ID NO: 5 | Nega |
| 12,13 | SEQ ID NO: 8 | SEQ ID NO: 23 | SEQ ID NO: 6 | $10^3$ copies |
| 14 | SEQ ID NO: 8 | SEQ ID NO: 23 | SEQ ID NO: 6 | Nega |
| 15,16 | SEQ ID NO: 9 | SEQ ID NO: 23 | SEQ ID NO: 6 | $10^3$ copies |
| 17 | SEQ ID NO: 9 | SEQ ID NO: 23 | SEQ ID NO: 6 | Nega |
| 18,19 | SEQ ID NO: 10 | SEQ ID NO: 23 | SEQ ID NO: 6 | $10^3$ copies |
| 20 | SEQ ID NO: 10 | SEQ ID NO: 23 | SEQ ID NO: 6 | Nega |
| 1,11 | DNA molecular weight marker ($\phi$×174/*Hae* III digest) | | | |

Fig. 5

| Lane | First primer | Second primer | Third oligonucleotide | Target RNA |
|---|---|---|---|---|
| 2,3 | SEQ ID NO: 9 | SEQ ID NO: 24 | SEQ ID NO: 7 | $10^3$ copies |
| 4 | SEQ ID NO: 9 | SEQ ID NO: 24 | SEQ ID NO: 7 | Nega |
| 5,6 | SEQ ID NO: 10 | SEQ ID NO: 24 | SEQ ID NO: 7 | $10^3$ copies |
| 7 | SEQ ID NO: 10 | SEQ ID NO: 24 | SEQ ID NO: 7 | Nega |
| 8,9 | SEQ ID NO: 11 | SEQ ID NO: 24 | SEQ ID NO: 7 | $10^3$ copies |
| 10 | SEQ ID NO: 11 | SEQ ID NO: 24 | SEQ ID NO: 7 | Nega |
| 12,13 | SEQ ID NO: 13 | SEQ ID NO: 25 | SEQ ID NO: 11 | $10^3$ copies |
| 14 | SEQ ID NO: 13 | SEQ ID NO: 25 | SEQ ID NO: 11 | Nega |
| 1,11 | DNA molecular weight marker ($\phi$×174/Hae III digest) | | | |

Fig. 6

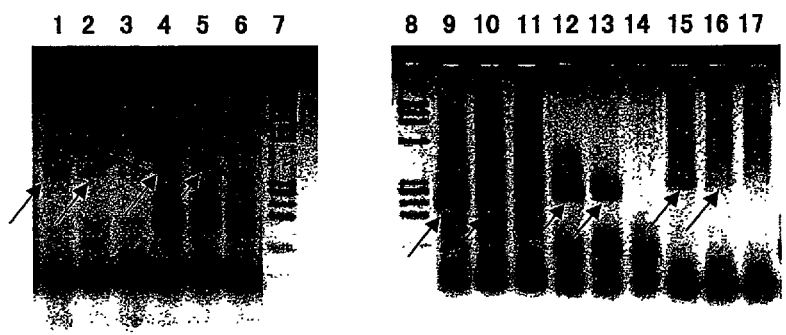

| Lane | First primer | Second primer | Third oligonucleotide | Target RNA |
|------|--------------|---------------|-----------------------|------------|
| 1,2 | SEQ ID NO: 17 | SEQ ID NO: 26 | SEQ ID NO: 13 | $10^3$ copies |
| 3 | SEQ ID NO: 17 | SEQ ID NO: 26 | SEQ ID NO: 13 | Nega |
| 4,5 | SEQ ID NO: 18 | SEQ ID NO: 26 | SEQ ID NO: 13 | $10^3$ copies |
| 6 | SEQ ID NO: 18 | SEQ ID NO: 26 | SEQ ID NO: 13 | Nega |
| 9,10 | SEQ ID NO: 16 | SEQ ID NO: 27 | SEQ ID NO: 14 | $10^3$ copies |
| 11 | SEQ ID NO: 16 | SEQ ID NO: 27 | SEQ ID NO: 14 | Nega |
| 12,13 | SEQ ID NO: 17 | SEQ ID NO: 27 | SEQ ID NO: 14 | $10^3$ copies |
| 14 | SEQ ID NO: 17 | SEQ ID NO: 27 | SEQ ID NO: 14 | Nega |
| 15,16 | SEQ ID NO: 18 | SEQ ID NO: 27 | SEQ ID NO: 14 | $10^3$ copies |
| 17 | SEQ ID NO: 18 | SEQ ID NO: 27 | SEQ ID NO: 14 | Nega |
| 7,8 | DNA molecular weight marker ($\phi$×174/*Hae* III digest) | | | |

OLIGONUCLEOTIDE FOR DETECTION OF HIV-1 AND DETECTION METHOD

The present invention relates to oligonucleotides used for detection of HIV-1 RNA in clinical tests and diagnoses.

Human immunodeficiency virus (HIV) is the pathogen of acquired immunodeficiency syndrome (AIDS). Two subtypes of HIV are known: HIV-1, which is spread worldwide, and HIV-2, which is epidemic mainly on the African West coast. The similarity between HIV-2 and simian immunodeficiency virus (SIV) in base sequence implies that HIV-2 may be zoonotic. However, clinical conditions of HIV-2 infection are less serious than those of HIV-1 infection.

HIV-1 infection induces production of antibodies against structural proteins and regulatory proteins of HIV-1. HIV-1 attacks the T cells classified as CD4+ lymphocytes as the main target immunocytes and hence abnormalizes the immune system in various ways. In the advanced stages of HIV-1 infection, B cells are stimulated to set off hypergammaglobulinemia, and autoantibodies and immunocomplexes appear with marked reduction of lymphocytes and blood platelets. Complications such as tuberculosis, *Pneumocystis carinii* pneumonia and other opportunistic infections at high levels of immunodeficiency induced by HIV-1 infection are diagnostic of onset of AIDS.

For diagnosis of HIV-1 infection, EIA (enzyme immunoassay) based on calorimetric detection of the reaction of an antibody against an viral antigen is available, coupled with Western blot confirmation of suspected positive serum samples by the presence of antibodies in the serum samples which react to a specific virus antigen in a blot of electrophoretically separated various virus particle antigens. However, assay methods which detect antibodies like this are not available for diagnoses of early stage infection before production of antibodies.

As discussed above, conventional assay methods can not afford diagnoses in the early stage of infection, require complicated operations and long time and can hardly detect a trace of HIV-1 in a sample in a short time. Therefore, development of a speedy and sensitive detection method is demanded. Especially, quantification of HIV-1 RNA is critical to get information on pathological progress and the effectiveness of anti-HIV drugs. Further, development of automatic analyzers is demanded to facilitate clinical tests.

For high sensitive detection, it is preferred to amplify a specific sequence in a gene to be detected or identified or an RNA derived from such a gene before the detection. As a method of amplifying a specific sequence in RNAs like the HIV-1 genomic RNA, the reverse transcription-polymerase chain reaction (RT-PCR) is known. In this method, the reverse transcription step for synthesis of the cDNA of the target DNA is followed by repeated cycles of heat denaturation, primer-annealing and elongation reaction in the presence of a couple of primers, one of which is complementary to either end of it the specific sequence and the other is homologous to the other end of the specific sequence (the antisense primer may be the same as the primer used in the reverse transcription step), and a thermostable DNA polymerase to give DNA as the amplification product of the specific sequence.

However, the necessity to conduct the operations in two steps (the reverse transcription step and the PCR step) and repeat the cumbersome operations such as rapid heating and cooling hinders automation of the RT-PCR.

NASBA or 3SR is known as a technique for amplifying a specific RNA sequence by the cooperative action of a reverse transcriptase and an RNA polymerase. This technique activates the chain reaction comprising synthesis of a double-stranded DNA having a promoter sequence from the target RNA by using a primer having a promoter sequence, a reverse transcriptase and ribonuclease H, and formation of an RNA polymerase of an RNA having the specific base sequence, which is then used as the template for synthesis of the above-mentioned double-stranded DNA having the promoter sequence. NASBA or 3SR allows relatively isothermal amplification of nucleic acid and is considered suitable for automation.

However, since the reactions involved in this amplification technique are carried out at relatively low temperatures (for example, at 41° C.), it is possible that the formation of an intramolecular structure of the target RNA lowers the reaction efficiency by hindering binding of the primers. Therefore, an operation of destroying the intramolecular structure of the target RNA such as heat denaturation of the target RNA are necessary before the amplification reaction to increase the binding efficiency of the primers.

The present invention provides an oligonucleotide which can hybridize with the specific site present in the intramolecularly free regions of the target RNA as a primer which can efficiently bind to the target RNA without heat denaturation of the target RNA. Specifically, the object of the present invention is to provide a simple, speedy and sensitive detection method through provision of an oligonucleotide for detection of HIV-1 RNA which can bind to an intramolecularly free region of the genomic RNA of HIV-1 at relatively low and constant temperatures (at 35° C. to 50° C., preferably at 41° C.), namely during amplification of a nucleic acid.

The present invention has been accomplished to attain the above-mentioned object. The invention defined in Claim 1 of the present application provides an oligonucleotide useful for detection of an RNA derived from HIV-1 consisting of at least 10 consecutive bases in any of SEQ ID NOS:1, 2, 4 to 10 and 13 to 17, which can bind to a specific site of the RNA. The invention defined in Claim 2 of the present application provides the oligonucleotide according to Claim 1, which is an oligonucleotide primer for DNA elongation. The invention defined in Claim 3 of the present application provides the oligonucleotide according to Claim 1, which is an oligonucleotide probe which is partly modified or labeled with a detectable label.

The invention defined in Claim 4 of the present application provides a step of amplifying an RNA derived from HIV-1, which comprises synthesizing a cDNA by the action of an RNA-dependent DNA polymerase by using a specific sequence in an RNA derived from HIV-1 anticipated in a sample as a template, a first primer containing a sequence complementary to the specific sequence and a second primer containing a sequence homologous to the specific sequence (either of which additionally has a promoter sequence for the RNA polymerase at the 5' end), denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA by the action of a DNA-dependent DNA polymerase, and then transcribing the double-stranded DNA into an RNA transcript, which acts as a template in the subsequent cDNA synthesis by the RNA-dependent DNA polymerase, in the presence of an RNA polymerase, wherein the first primer is an oligonucleotide consisting of at least 10 consecutive bases in any of SEQ ID NOS:1, 2, 4 to 10 and 13 to 17, and the second primer is an oligonucleotide consisting of at least 10 consecutive bases in any of SEQ ID NOS: 19 to 27.

The invention defined in Claim 5 of the present application provides the step according to Claim 4, wherein the combination of the first primer and the second primer is any of the following combinations.

TABLE 1

| | The first primer | The second primer |
|---|---|---|
| 1 | SEQ ID NO: 5 | SEQ ID NO: 19 |
| 2 | SEQ ID NO: 5 | SEQ ID NO: 20 |
| 3 | SEQ ID NO: 6 | SEQ ID NO: 20 |
| 4 | SEQ ID NO: 5 | SEQ ID NO: 21 |
| 5 | SEQ ID NO: 6 | SEQ ID NO: 21 |
| 6 | SEQ ID NO: 8 | SEQ ID NO: 22 |
| 7 | SEQ ID NO: 9 | SEQ ID NO: 22 |
| 8 | SEQ ID NO: 10 | SEQ ID NO: 22 |
| 9 | SEQ ID NO: 8 | SEQ ID NO: 23 |
| 10 | SEQ ID NO: 9 | SEQ ID NO: 23 |
| 11 | SEQ ID NO: 10 | SEQ ID NO: 23 |
| 12 | SEQ ID NO: 9 | SEQ ID NO: 24 |
| 13 | SEQ ID NO: 10 | SEQ ID NO: 24 |
| 14 | SEQ ID NO: 11 | SEQ ID NO: 24 |
| 15 | SEQ ID NO: 13 | SEQ ID NO: 25 |
| 16 | SEQ ID NO: 17 | SEQ ID NO: 26 |
| 17 | SEQ ID NO: 18 | SEQ ID NO: 26 |
| 18 | SEQ ID NO: 16 | SEQ ID NO: 27 |
| 19 | SEQ ID NO: 17 | SEQ ID NO: 27 |
| 20 | SEQ ID NO: 18 | SEQ ID NO: 27 |

The invention defined in Claim 6 of the present application provides the step according to Claim 4, which further comprises adding a third oligonucleotide which is complementary to a region of the RNA derived from HIV-1 which flanks the 5' end of the specific sequence with an overlap (of from 1 to 10 bases) with the specific sequence to form a template used in the initial stage of the amplification by cutting the RNA derived from HIV-1 at the 5' end of the specific sequence (by the action of the rebonuclease H), wherein the combination of the first primer, the second primer and the third primer is any of the following combinations.

TABLE 2

| | The first primer | The second primer | The third primer |
|---|---|---|---|
| 1 | SEQ ID NO: 5 | SEQ ID NO: 19 | SEQ ID NO: 2 |
| 2 | SEQ ID NO: 5 | SEQ ID NO: 20 | SEQ ID NO: 3 |
| 3 | SEQ ID NO: 6 | SEQ ID NO: 20 | SEQ ID NO: 3 |
| 4 | SEQ ID NO: 5 | SEQ ID NO: 21 | SEQ ID NO: 4 |
| 5 | SEQ ID NO: 6 | SEQ ID NO: 21 | SEQ ID NO: 4 |
| 6 | SEQ ID NO: 8 | SEQ ID NO: 22 | SEQ ID NO: 5 |
| 7 | SEQ ID NO: 9 | SEQ ID NO: 22 | SEQ ID NO: 5 |
| 8 | SEQ ID NO: 10 | SEQ ID NO: 22 | SEQ ID NO: 5 |
| 9 | SEQ ID NO: 8 | SEQ ID NO: 23 | SEQ ID NO: 6 |
| 10 | SEQ ID NO: 9 | SEQ ID NO: 23 | SEQ ID NO: 6 |
| 11 | SEQ ID NO: 10 | SEQ ID NO: 23 | SEQ ID NO: 6 |
| 12 | SEQ ID NO: 9 | SEQ ID NO: 24 | SEQ ID NO: 7 |
| 13 | SEQ ID NO: 10 | SEQ ID NO: 24 | SEQ ID NO: 7 |
| 14 | SEQ ID NO: 11 | SEQ ID NO: 24 | SEQ ID NO: 7 |
| 15 | SEQ ID NO: 13 | SEQ ID NO: 25 | SEQ ID NO: 11 |
| 16 | SEQ ID NO: 17 | SEQ ID NO: 26 | SEQ ID NO: 13 |
| 17 | SEQ ID NO: 18 | SEQ ID NO: 26 | SEQ ID NO: 13 |
| 18 | SEQ ID NO: 16 | SEQ ID NO: 27 | SEQ ID NO: 14 |
| 19 | SEQ ID NO: 17 | SEQ ID NO: 27 | SEQ ID NO: 14 |
| 20 | SEQ ID NO: 18 | SEQ ID NO: 27 | SEQ ID NO: 14 |

The invention defined in Claim 7 of the present application provides a step of detecting HIV-1, which comprises conducting a step as defined in any of Claims 4 to 6 in the presence of an oligonucleotide probe (having a sequence different from those of the first primer and the second primer) which can specifically bind to the RNA transcript resulting from the amplification and is labeled with an fluorescent intercalative dye, and measuring the change in the fluorescence from the reaction solution. The invention defined in Claim 8 of the present application provides the step according to Claim 7, wherein the oligonucleotide probe is designed to hybridize with at least part of the RNA transcript and alters its fluorescence upon hybridization.

Figure 1:
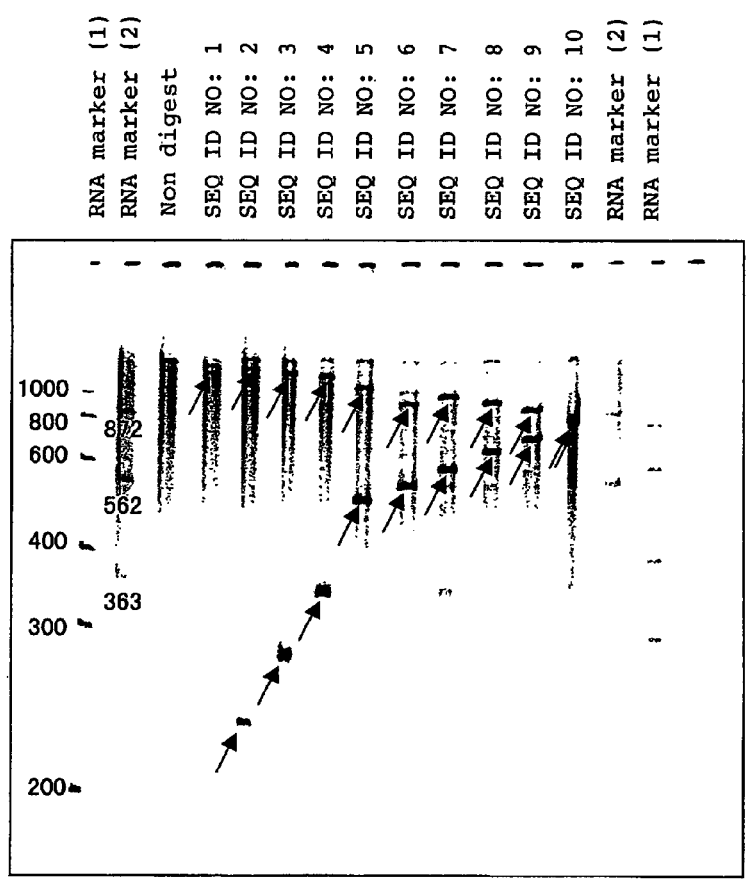
FIG. 1 is a (negative) photograph showing the results of urea-denatured 6% PAGE of samples after binding tests on oligonucleotides SEQ ID NOS: 1 to 10 for binding to HIV-1 RNA at 41° C.

FIG. 3 is an electrophoretogram showing the results of RNA amplification from the initial RNA amount of $10^3$ copies/30 μl in Example 2 using oligonucleotides in combinations (1) to (5) shown in Table 4. Lanes 1 and 2: combination (1). Lanes 6 and 7: combination (2). Lanes 9 and 10: combination (3). Lanes 13 and 14: combination (4). Lanes 16 and 17: combination (5). Lanes 3, 8, 11, 15 and 18: Nega (diluent only instead of the RNA sample). The molecular weight marker, φX174/HaeIII digest (Marker 4) was used (lanes 4, 5 and 12). All the combinations gave specific bands (indicated by arrows).

FIG. 4 is an electrophoretogram showing the results of RNA amplification from the initial RNA amount of $10^3$ copies/30 μl in Example 2 using oligonucleotides in combinations (6) to (11) shown in Table 4. Lanes 2 and 3: combination (6). Lanes 5 and 6: combination (7). Lanes 8 and 9: combination (8). Lanes 12 and 13: combination (9). Lanes 15 and 16: combination (10). Lanes 18 and 19: combination (11). Lanes 4, 7, 10, 14, 17 and 20: Nega (diluent only instead of the RNA sample). The molecular weight marker, φX174/HaeIII digest (Marker 4) was used (lanes 1 and 11). All the combinations gave specific bands.

FIG. 5 is an electrophoretogram showing the results of RNA amplification from the initial RNA amount of $10^3$ copies/30 μl in Example 2 using oligonucleotides in combinations (12) to (15) shown in Table 4. Lanes 2 and 3: combination (12). Lanes 5 and 6: combination (13). Lanes 8 and 9: combination (14). Lanes 12 and 13: combination (15). Lanes 4, 7, 10 and 14: Nega (diluent only instead of the RNA sample). The molecular weight marker, φX174/HaeIII digest (Marker 4) was used (lanes 1 and 11). All the combinations gave specific bands.

FIG. 6 is an electrophoretogram showing the results of RNA amplification from the initial RNA amount of $10^3$ copies/30 μl in Example 2 using oligonucleotides in combinations (16) to (20) shown in Table 4. Lanes 1 and 2: combination (16). Lanes 4 and 5: combination (17). Lanes 9 and 10: combination (18). Lanes 12 and 13: combination (19). Lanes 15 and 16: combination (20). Lanes 3, 6, 11, 14 and 17: Nega (diluent only instead of the RNA sample). The molecular weight marker, φX174/HaeIII digest (Marker 4) was used (lanes 7 and 8). All the combinations gave specific bands.

Figure 7:
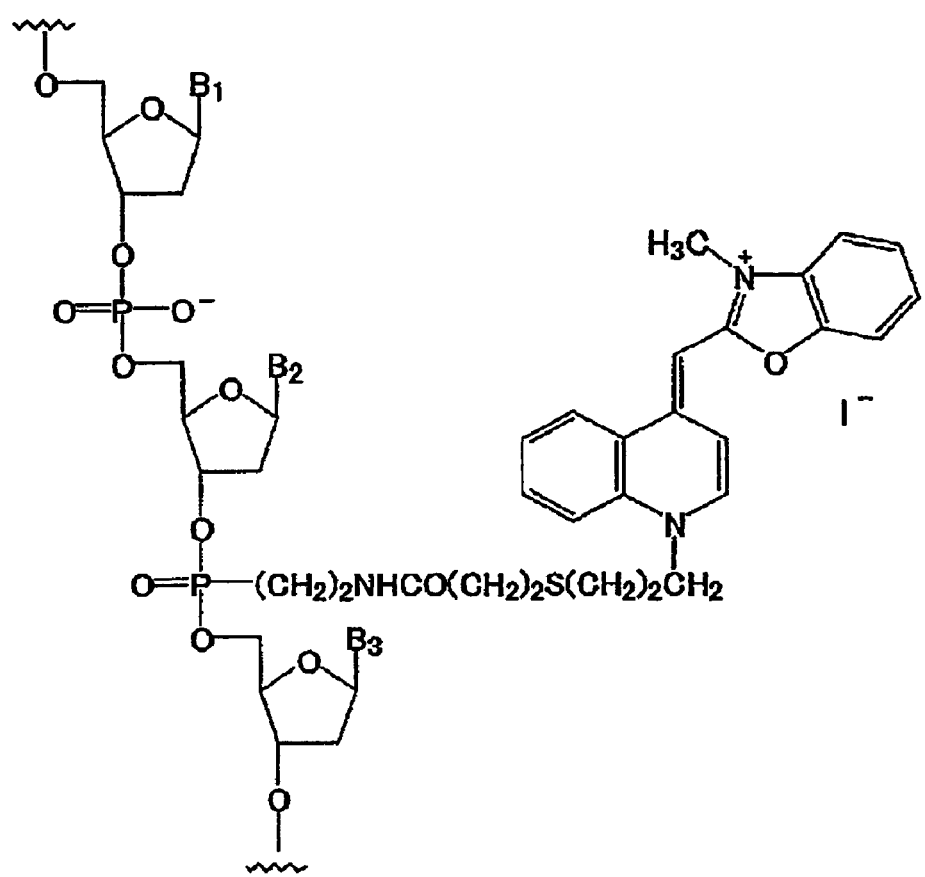

FIG. 7 is the chemical formula of the fluorescent intercalative dye moiety of the fluorescent intercalative dye-labeled oligonucleotide used in Example 3. $B_1$ to $B_3$ are nucleic acid bases.

Figure 8:
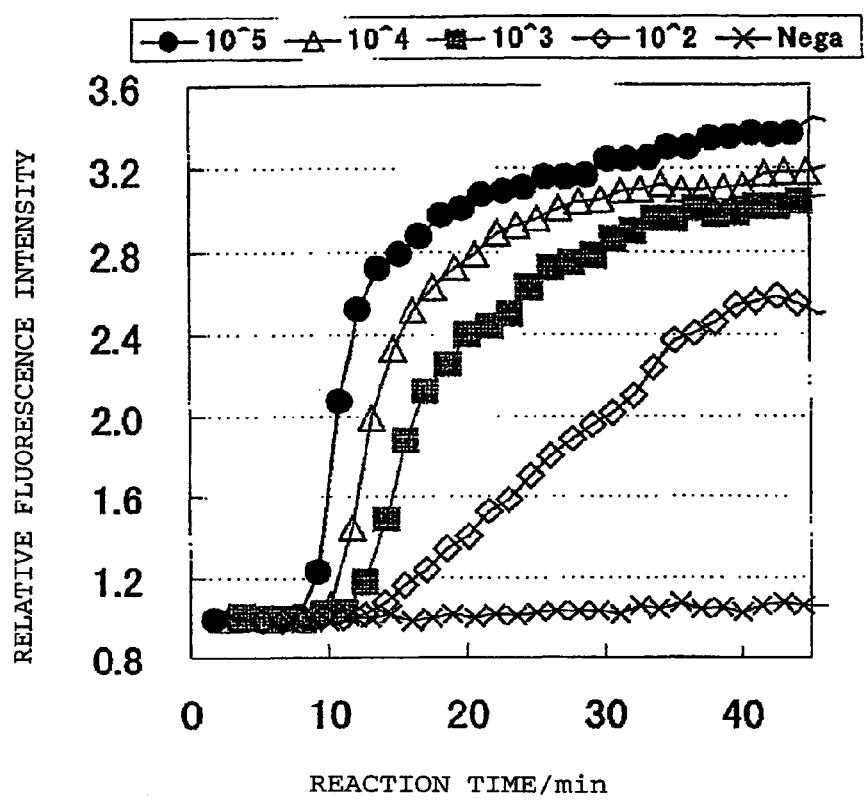

FIG. 8 is a graph correlating the reaction time and the fluorescence enhancement accompanying RNA synthesis at initial RNA amounts of $10^5$ copies/30 μl to $10^2$ copies/30 μl in Example 2. Nega indicates a sample prepared by using a diluent instead of the RNA sample.

Now, the present invention will be described in detail.

The oligonucleotide of the present invention consists of at least 10 consecutive bases in any of SEQ ID NOS:1, 2, 4 to 10 and 13 to 17. The oligonucleotide is useful for detection of an genomic RNA of HIV-1, can bind to a specific site of the HIV-1 RNA, especially at relatively low and constant temperatures (from 35° C. to 50° C., preferably 41° C.). Specifically, the oligonucleotide of the present invention is useful for amplification of the RNA by NASBA or the like and for detection of the target nucleic acid without or after such amplification and makes it possible to provide a simple, speedy and sensitive detection method for clinical diagnosis. Namely, the present invention provides a nucleic acid amplification step for amplification of HIV-RNA in a sample, and a method of detecting the RNA transcript formed by the nucleic acid amplification step. The amplification step of the present invention covers any amplification methods such as PCR, NASBA or 3SR. However, isothermal nucleic acid amplification such as NASBA or 3SR by the cooperative action of a reverse transcriptase and an RNA polymerase (under such conditions that the reverse transcriptase and the RNA polymerase act cooperatively) is preferred for amplifying a specific RNA sequence in HIV-1.

For example, NASBA amplification of an RNA comprises synthesizing a cDNA by the action of an RNA-dependent DNA polymerase by using a specific sequence in HIV-1 RNA in a sample as the template, denuding the cDNA to a single-stranded DNA through degradation of the RNA in the resulting RNA-DNA double strand by ribonuclease H, forming a double-stranded DNA having a promoter sequence which can be transcribed into an RNA consisting of the specific base sequence or a sequence complementary to the specific base sequence by using the single-stranded DNA by the action of a DNA-dependent DNA polymerase, and then transcribing the double-stranded DNA into an RNA transcript, which acts as a template in the subsequent cDNA synthesis by the RNA-dependent DNA polymerase, in the presence of an RNA polymerase. The present invention is characterized by the use of a first oligonucleotide primer consisting of at least 10 consecutive bases in any of SEQ ID NOS:1, 2, 4 to 10 and 13 to 17, which can bind to a specific site of the HIV-1 RNA and a second oligonucleotide consisting of at least 10 consecutive bases in any of SEQ ID NOS: 19 to 27 containing a sequence homologous to part of the HIV-1 RNA to be amplified (either of which additionally has a promoter sequence for the RNA polymerase at the 5' end).

One embodiment of the present invention is the above-mentioned amplification step wherein the combination of the first primer and the second primer is oligonucleotide primers consisting of at least 10 consecutive bases in any set of sequences shown in Table 1 (wherein either of them additionally has a promoter sequence for the RNA polymerase at the 5' end). The RNA-dependent DNA polymerase, the DNA-dependent DNA polymerase and the ribonuclease H are not particularly limited, but AMV reverse transcriptase is preferable because it has the activities of all of them. As the RNA polymerase, T7 phage RNA polymerase or SP6 phage RNA polymerase is preferred, though there is no particular restriction.

In the above-mentioned amplification step, even if the specific sequence is not present at the 5' end, HIV-1 RNA can be amplified by adding an oligonucleotide complementary to a region of HIV-1 RNA which flanks the 5' end of the specific sequence with an overlap (of from 1 to 10 bases) with the specific sequence to cleave HIV-1 RNA at the 5' end (by the action of a ribonuclease H) before it is used as the template in the initial stage of the nucleic acid amplification. As the scissor oligonucleotide, an oligonucleotide of any of SEQ ID NOS: 1, 2, 4 to 10 and 13 to 17 (which is not used as the first oligonucleotide in the above-mentioned amplification step) may be used. The scissor oligonucleotide is preferred to have a chemically modified hydroxyl group (for example, an aminated hydroxyl group) at the 3' end not to elongate from the 3' end.

When the third oligonucleotide complementary to a region which flanks the 5' end of the specific sequence with a (1 to 10-base) overlap with the specific sequence as mentioned above is added to cleave HIV-1 RNA at the 5' end (by the action of a ribonuclease H) before it is used as the template in the initial stage of the nucleic acid amplification, the combination of the first primer, the second primer and the third primer is preferably a set of oligonucleotide primers consisting of at least 10 consecutive bases in any set of sequences shown in Table 2. In this case, the third oligonucleotide (the scissor oligonucleotide) is preferred to have a chemically modified hydroxyl group (for example, an aminated hydroxyl group) at the 3' end not to elongate from the 3' end, too.

Detection of the amplification product obtained in the nucleic acid amplification step is preferably carried out by measuring the change in the fluorescence of the reaction solution during the amplification step in the presence of an oligonucleotide probe labeled with a fluorescent intercalative dye, though it can be detected by conventional methods for detection of nucleic acid. The oligonucleotide probe may be, for example, an oligonucleotide having a fluorescent intercalative dye linked to a phosphorus atom via a linker. Such a preferable probe alters its fluorescence upon formation of a double strand with the target nucleic acid (a complementary nucleic acid) through intercalation of the intercalator moiety to the double strand (Ishiguro, T. et al., (1996) Nucleic Acids Res. 24 (24) 4992–4997).

The sequence of the probe is not particularly limited as long as it contains a sequence complementary to at least part of the RNA transcript. For example, when the combination of a first primer of SEQ ID NO: 17 and a second primer of SEQ ID NO: 27 (either of which additionally has a promoter sequence for an RNA polymerase at the 5' end) is used in the RNA amplification step, a sequence consisting of or complementary to at least 10 consecutive bases in SEQ ID NO: 28 may be mentioned. When the combination of a first primer of SEQ ID NO: 5 and a second primer of SEQ ID NO: 21 (either of which additionally has a promoter primer for an RNA polymerase at the 5' end) is used, a sequence consisting of or complementary to at least 10 consecutive bases in SEQ ID NO: 29 may be mentioned. In this case, it is preferred to chemically modify the hydroxyl group at the 3' end of the probe (for example, by adding glycolic acid) to prevent elongation reaction using the probe as a primer.

By carrying out the amplification step in the presence of the above-mentioned probe, amplification and detection of an RNA having the same sequence as a specific sequence in HIV-1 RNA can be carried out at constant temperature in one tube in one step and can be automated easily.

Now, the present invention will be described in further detail by referring to Examples. However, the present invention is by no means restricted to these specific Examples.

EXAMPLE 1

It was verified whether oligonucleotides of SEQ ID NOS: 1 to 18 bind to specific sites of HIV-1 RNA at 41° C.

(1) A 1628-nt RNA base sequence in the HIV-1 RNA base sequence containing the structural gene of the core protein (gag) was used as a standard RNA. The standard RNA was obtained by conventional extraction of HIV-1 RNA with ACCRUN (product name) 315, HIV-1 RNA Positive Control, Series 400 (BBI (Boston Biomedica, Inc.) and synthesis of a double-stranded DNA containing a base sequence from the gag region by RT-PCR and in vitro transcription using the DNA as the template and purified.

The standard RNA was quantified by UV absorptiometry at 260 nm and diluted to 0.43 pmol/µl with an RNA diluent (10 mM Tris-HCl (pH 8.0), 0.1 mM EDTA, 1 mM DTT, 0.5 U/µl RNase inhibitor).

(2) 14.0 µl portions of a reaction solution of the following composition were dispensed into PCR tubes (capacity 0.5 ml: Gene Amp Thin-Walled Reaction Tubes, Perkin Elmer).

The composition of the reaction solution

| | |
|---|---|
| 20.0 mM | Tris-HCl buffer (pH 7.5) |
| 20.0 mM | Potassium chloride |
| 10.0 mM | Magnesium chloride |
| 0.1 mM | DTT |
| 0.1 mM | EDTA |
| 1.3 µM | Standard RNA |
| 1.3 µM | Oligonucleotide solution (a solution of an oligonucleotide of any of SEQ ID NOS: 1 to 18) |

Distilled Water for Volume Adjustment (3) The reaction solutions were incubated at 41° C. for 5 minutes, and 1 µl of an RNase H (0.1 U/µl) (Takara Shuzo Co., Ltd.) (which cleaves the RNA strand in an DNA/RNA double strand) was added.

(4) The PCR tubes were incubated at 41° C. for 15 minutes again.

(5) The cleavage fractions obtained by the reaction were identified by urea-denatured polyacrylamide gel electrophoresis (polyacrylamide concentration 6%, urea 7 M) followed by staining with a commercial stain solution (trade name SYBR Green II, Takara Shuzo Co., Ltd.). The cleavage of the target RNA by the action of the RNase on the RNA strand in the DNA/RNA double strand formed by hybridization of an oligonucleotide with a specific region of the target RNA can be confirmed by the appearance of specific bands.

(6) As the RNA markers, Perfect RNA Markers, 0.1–1 Kb (RNA marker (1)) and Perfect RNA Markers, 0.36–9.5 Kb (RNA marker (2)) (Novagen) were used.

Figure 2:
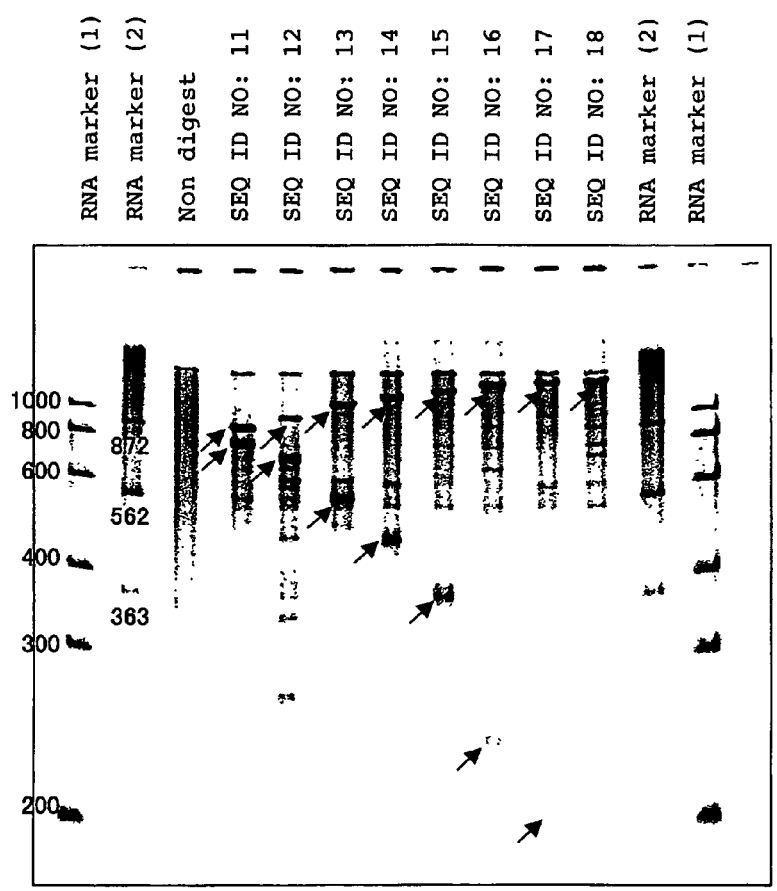
FIG. 2 is a (negative) photograph showing the results of urea-denatured 6% PAGE of samples after binding tests on oligonucleotides SEQ ID NOS: 11 to 18 for binding to HIV-1 RNA at 41° C.

The results (negative photographs) of the electrophoresis are shown in FIG. 1 (SEQ ID NOS: 1 to 10) and FIG. 2 (SEQ ID NOS: 11 to 18). The regions of the target RNA which formed hybrids with oligonucleotides were degraded by the RNase H to give degradation products of specific lengths. Table 3 shows the lengths of the bands which were supposed to be formed by the degradation of specific sites of the target RNA upon binding of oligonucleotides. In each case, specific bands (indicated in the figures by arrows) which indicate strong binding of these oligonucleotides to HIV-1 RNA at a constant temperature of 41° C. were observed.

TABLE 3

| SEQ ID NO of oligonucleotide | Length of supposed band (nt) |
|---|---|
| SEQ ID NO: 1 | 120, 1508 |
| SEQ ID NO: 2 | 216, 1412 |
| SEQ ID NO: 3 | 267, 1361 |
| SEQ ID NO: 4 | 331, 1297 |
| SEQ ID NO: 5 | 489, 1139 |
| SEQ ID NO: 6 | 532, 1096 |
| SEQ ID NO: 7 | 581, 1047 |
| SEQ ID NO: 8 | 646, 982 |
| SEQ ID NO: 9 | 706, 922 |
| SEQ ID NO: 10 | 803, 825 |
| SEQ ID NO: 11 | 779, 849 |
| SEQ ID NO: 12 | 701, 927 |
| SEQ ID NO: 13 | 562, 1066 |
| SEQ ID NO: 14 | 468, 1160 |
| SEQ ID NO: 15 | 381, 1247 |
| SEQ ID NO: 16 | 259, 1369 |
| SEQ ID NO: 17 | 224, 1404 |
| SEQ ID NO: 18 | 190, 1438 |

Table 3 shows the sequences of the oligonucleotides used in the present example and bands which were supposed to appear in the binding tests using them.

EXAMPLE 2

RNA amplification was carried out using oligonucleotides which bind to specific sites of HIV-1 RNA.

(1) The same standard HIV-1 RNA as used in Example 1 was diluted to $10^3$ copies/5 µl with an RNA diluent (10 mM Tris-HCl (pH 8.0), 1 mM EDTA, 0.5 U/µl RNase inhibitor (Takara Shuzo Co., Ltd.), 5 mM DTT). The diluent alone was used as a control sample (Nega).

(2) 20.8 µl portions of a reaction solution of the following composition were dispensed into 0.5 ml PCR tubes (Gene Amp Thin-Walled Reaction Tubes, Perkin Elmer), and 5 µl of the RNA sample was added.

The composition of the reaction solution (in terms of the concentrations in the final volume of 30 µl)

| | |
|---|---|
| 60 mM | Tris-HCl buffer (pH 8.6) |
| 13 mM | Magnesium chloride |
| 100 mM | Potassium chloride |
| 39 U | RNase Inhibitor |
| 1 mM | DTT |
| 0.25 mM | each of dATP, dCTP, dGTP and dTTP |
| 3.6 mM | ITP |
| 3.0 mM | each of ATP, CTP, GTP and UTP |
| 1.0 µM | First primer |
| 1.0 µM | Second primer |
| 0.16 µM | Third oligonucleotide |
| 13% | DMSO |

Distilled Water for Volume Adjustment (3) RNA amplification was carried out in the solutions prepared in (2) which contained the combinations of a first primer, a second primer and a third oligonucleotide shown in Table 4.

(4) The reaction solutions were incubated at 41° C. for 5 minutes, and 4.2 µl of an enzyme solution of the following composition was added.

The composition of the enzyme solution (in terms of the concentrations in the final volume of 30 µl)

| | |
|---|---|
| 1.7% | Sorbitol |
| 3 µg | Bovine serum albumin |
| 142 U | T7 RNA polymerase (GIBCO) |
| 8 U | AMV reverse transcriptase (Takara Shuzo Co., Ltd.) |

Distilled Water for Volume Adjustment (5) The PCR tubes were incubated at 41° C. for 30 minutes again.

(6) The sites of the RNA amplified in the reaction were identified by agarose gel electrophoresis (agarose concentration 4%) followed by staining with SYBR Green II (Takara Shuzo Co., Ltd.). The RNA segments between the first and second primers were amplified subsequent to the binding of oligonucleotides to specific regions of the target RNA and detected as specific bands.

The results (negative photographs) of the electrophoresis are shown in FIGS. 3 to 6. The lengths of the products of the amplification reaction observed as specific bands are shown in Table 4. The RNA amplification reactions using any combinations of oligonucleotides shown in Table 4 gave specific bands and proved to be useful for detection of HIV-1 RNA.

TABLE 4

| Combi-nation | First primer | Second primer | Third oligonucleotide | Amplification product |
|---|---|---|---|---|
| (1) | SEQ ID NO: 5 | SEQ ID NO: 19 | SEQ ID NO: 2 | 306 nt |
| (2) | SEQ ID NO: 5 | SEQ ID NO: 20 | SEQ ID NO: 3 | 255 nt |
| (3) | SEQ ID NO: 6 | SEQ ID NO: 20 | SEQ ID NO: 3 | 298 nt |
| (4) | SEQ ID NO: 5 | SEQ ID NO: 21 | SEQ ID NO: 4 | 191 nt |
| (5) | SEQ ID NO: 6 | SEQ ID NO: 21 | SEQ ID NO: 4 | 234 nt |
| (6) | SEQ ID NO: 8 | SEQ ID NO: 22 | SEQ ID NO: 5 | 190 nt |
| (7) | SEQ ID NO: 9 | SEQ ID NO: 22 | SEQ ID NO: 5 | 250 nt |
| (8) | SEQ ID NO: 10 | SEQ ID NO: 22 | SEQ ID NO: 5 | 347 nt |
| (9) | SEQ ID NO: 8 | SEQ ID NO: 23 | SEQ ID NO: 6 | 147 nt |
| (10) | SEQ ID NO: 9 | SEQ ID NO: 23 | SEQ ID NO: 6 | 207 nt |
| (11) | SEQ ID NO: 10 | SEQ ID NO: 23 | SEQ ID NO: 6 | 304 nt |
| (12) | SEQ ID NO: 9 | SEQ ID NO: 24 | SEQ ID NO: 7 | 158 nt |
| (13) | SEQ ID NO: 10 | SEQ ID NO: 24 | SEQ ID NO: 7 | 255 nt |
| (14) | SEQ ID NO: 11 | SEQ ID NO: 24 | SEQ ID NO: 7 | 301 nt |
| (15) | SEQ ID NO: 13 | SEQ ID NO: 25 | SEQ ID NO: 11 | 227 nt |
| (16) | SEQ ID NO: 17 | SEQ ID NO: 26 | SEQ ID NO: 13 | 348 nt |
| (17) | SEQ ID NO: 18 | SEQ ID NO: 26 | SEQ ID NO: 13 | 382 nt |
| (18) | SEQ ID NO: 16 | SEQ ID NO: 27 | SEQ ID NO: 14 | 219 nt |
| (19) | SEQ ID NO: 17 | SEQ ID NO: 27 | SEQ ID NO: 14 | 254 nt |
| (20) | SEQ ID NO: 18 | SEQ ID NO: 27 | SEQ ID NO: 14 | 288 nt |

Table 4 show the combinations of the first and second primers and the third oligonucleotides used in the present Example and the lengths of the specific bands detected as the products of the RNA amplification using them. The third oligonucleotides had aminated hydroxyl groups at the 3' end. The second primers had base sequences (SEQ ID NO: 30) which additionally had the T7 promoter sequence at the 5' end (SEQ ID NO: 30 comprises the T7 promoter sequence from "A" at position 1 from the 5' end to "A" at position 22 and the subsequent enhancer sequence from "G" at position 23 to "A" at position 28).

EXAMPLE 3

The target HIV-RNA derived from various numbers of initial copies was detected using the combinations of oligonucleotides in the present invention.

(1) The same standard HIV-1 RNA as used in Example 1 was diluted to $10^5$–$10^2$ copies/5 µl with an RNA diluent (10 mM Tris-HCl (pH 8.0), 1 mM EDTA, 0.5 U/µl RNase inhibitor (Takara Shuzo Co., Ltd.), 5 mM DTT). The diluent alone was used as a control sample (negative).

20.8 µl portions of a reaction solution of the following composition were dispensed into 0.5 ml PCR tubes (Gene Amp Thin-Walled Reaction Tubes, Perkin Elmer), and 5 µl of the RNA sample was added.

The composition of the reaction solution (in terms of the concentrations in the final volume of 30 µl)

| | |
|---|---|
| 60 mM | Tris-HCl buffer (pH 8.6) |
| 17 mM | Magnesium chloride |
| 100 mM | Potassium chloride |
| 39 U | RNase Inhibitor |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 µM | Third oligonucleotide (SEQ ID NO: 14) |
| 1.0 µM | First primer (SEQ ID NO: 17) |
| 1.0 µM | Second primer (SEQ ID NO: 27) |

(which had a base sequence (SEQ ID NO: 30) including the T7 promoter sequence at the 5' end (SEQ ID NO: 30 comprises the T7 promoter sequence from "A" at position 1 from the 5' end to "A" at position 22 and the subsequent enhancer sequence from "G" at position 23 to "A" at position 28).

25 nM Oligonucleotide (SEQ ID NO:28) labeled with a fluorescent intercalative dye (FIG. 7)

(having the fluorescent intercalative dye between "A" at position 4 from the 5' end and "T" at position 5 and having a hydroxyl group modified with glycolic acid at the 3' end)

13% DMSO

Distilled Water for Volume Adjustment (3) The reaction solutions were incubated at 41° C. for 5 minutes, and 4.2 µl of an enzyme solution of the following composition which was pre-incubated at 41° C. for 2 minutes was added.

The composition of the enzyme solution (in terms of the concentrations in the final volume of 30 µl)

| | |
|---|---|
| 1.7% | Sorbitol |
| 3 µg | Bovine serum albumin |
| 142 U | T7 RNA polymerase (GIBCO) |
| 8 U | AMV reverse transcriptase (Takara Shuzo Co., Ltd.) |

Distilled Water for Volume Adjustment (4) The fluorescence intensities of the reaction solutions in the PCR tubes were directly monitored at 41° C. in a thermostatic fluorescent spectrophotometer at an excitation wavelength of 470 nm and an emission wavelength of 510 nm. The time courses of the ratio of fluorescence intensities of the samples (fluorescence intensity at a certain time/background fluorescence intensity) from addition of the enzyme solution at 0 minute were shown in FIG. 8. The initial amounts of the RNA were from $10^2$ copies/30 μl to $10^5$ copies/30 μl.

FIG. 8 demonstrates that it was possible to detect $10^2$ copies in about 15 minutes. The fluorescence profiles dependent on the initial concentrations of the standard RNA suggest that it is possible to quantify HIV-1 RNA in an unknown sample. Thus, it is proved that the present invention allows speedy and sensitive detection of HIV-1 RNA.

As described above, the present invention provides oligonucleotides useful for detection of the genomic RNA which can bind to specific sites of the RNA of HIV-1 (hybridize with intramolecularly free regions). The oligonucleotides can bind to HIV-1 RNA at relatively low and constant temperatures (at 35° C. to 50° C., preferably at 41° C.). The present invention also provides oligonucleotides for detection of HIV-1 RNA, i.e., oligonucleotide primers and oligonucleotide probes used in nucleic acid amplification.

The entire disclosure of Japanese Patent Application No. 2000-334937 filed on Oct. 30, 2000 including specification, claims, drawings and summary are incorporated herein by reference in its entirety.

The invention claimed is:

1. A method for amplifying an RNA derived from HIV-1, which comprises the steps:
   (A) incubating RNA of a sample suspected to contain said RNA in the presence of an RNA-dependent DNA polymerase under conditions sufficient to synthesize a cDNA-RNA molecule therefrom, wherein said incubation is conducted in the presence of a first primer containing a sequence complementary to a specific sequence of said RNA and a second primer containing a sequence homologous to the specific sequence either of which additionally has a promoter sequence for the RNA polymerase at the 5' end,
   (B) incubating said cDNA-RNA molecule in the presence of a ribonuclease H activity under conditions sufficient to degrade the RNA of said molecule thereby forming a single-stranded DNA molecule,
   (C) forming a double-stranded DNA molecule having a promoter sequence which can be transcribed into an RNA molecule comprising said specific base sequence or a sequence complementary to said specific base sequence by incubating said single-stranded DNA molecule in the presence of a DNA-dependent DNA polymerase, and
   (D) incubating said formed double-stranded DNA molecule in the presence of an RNA polymerase under conditions sufficient to produce an RNA transcript, wherein said RNA transcript acts as a template in a subsequent cDNA synthesis mediated by an RNA-dependent DNA polymerase,
   wherein said first primer is an oligonucleotide comprising at least 10 consecutive bases in any of SEQ ID NOS: 14 or 17, and the second primer is an oligonucleotide comprising at least 10 consecutive bases of SEQ ID NO: 27, to thereby amplify said RNA derived from HIV-1.

2. The method of claim 1, wherein an oligonucleotide comprising at least 10 consecutive bases in SEQ ID NO: 17 is employed as the first primer and an oligonucleotide comprising at least 10 consecutive bases in SEQ ID NO: 27 is employed as the second primer.

3. The method of claim 1, wherein step (A) further comprises providing an oligonucleotide that is complementary to a region of said RNA derived from HIV-1 that overlaps the 5' end of said specific sequence, wherein said provided oligonucleotide hybridizes to said RNA derived from HIV-1 to form a double-stranded nucleic acid molecule; wherein said ribonuclease H activity acts upon said double-stranded nucleic acid molecule to form a template by cutting the RNA derived from HIV-1 at the 5' end of said specific sequence, wherein an oligonucleotide comprising at least 10 consecutive bases in SEQ ID NO: 17 is employed as the first primer, an oligonucleotide comprising at least 10 consecutive bases in SEQ ID NO: 27 is employed as the second primer, and an oligonucleotide comprising at least 10 consecutive bases in SEQ ID NO: 14 is employed as said provided oligonucleotide.

4. The method of claim 3, wherein said overlap is from 1 to 10 bases.

5. The method of claim 1, wherein an oligonucleotide comprising at least 10 consecutive bases in SEQ ID NO: 14 is employed as the first primer and an oligonucleotide comprising at least 10 consecutive bases in SEQ ID NO: 27 is employed as the second primer.

6. A method for detecting HIV-1, which comprises conducting the method of any of claims 1 to 3 in the presence of an oligonucleotide probe having a sequence comprising at least 10 consecutive bases of SEQ ID NO:28, wherein said oligonucleotide probe specifically binds to said RNA transcript and is labeled with an fluorescent intercalative dye, and measuring any change in the fluorescence from the reaction solution.

* * * * *

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 1
ttccctttcg ctttcaagtc                                            20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 2
gtcaaaattt ttggcgtact                                            20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 3
cgcttaatac tgacgctctc                                            20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 4
aatttatatt ttttcttcc                                             20

<210> SEQ ID NO 5
<211> LENGTH: 20
```

```
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 5
ttgctactgt attatataat                                            20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 6
ttggtgtctt ttatctctat                                            20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 7 tttttttctta cttttgtttt                                           20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 8
tgcactatag ggtaattttg                                            20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 9
acccatgcat ttaaagttct                                            20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 10
tagcatggtg tttaaatctt                                            20

<210> SEQ ID NO 11
<211> LENGTH: 20
<212> TYPE: DNA
```

```
<213> ORGANISM: Artificial Sequence
<220> FEATURE:
<223> OTHER INFORMATION: Oligonucleotide hybridizable with a specific
      site of HIV-1 RNA

<400> SEQUENCE: 11
tctcttttaa catttgcatg                                                      20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 12
ctctcatctg gcctggtgca                                                      20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 13
attcttacta ttttatttaa                                                      20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 14
ctcggctctt agagttttat                                                      14

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 15
tgcttttaaa atagtcttac                                                      20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 16
attatggtag ctgtatttgt                                                      20

<210> SEQ ID NO 17
<211> LENGTH: 20
<212> TYPE: DNA
<213> ORGANISM: Artificial Sequence
```

```
<220> FEATURE:
<223> OTHER INFORMATION: Oligonucleotide hybridizable with a specific
      site of HIV-1 RNA

<400> SEQUENCE: 17
tctttctttg gttcctaaaa                                              20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide hybridizable with a specific
      site of HIV-1 RNA

<400> SEQUENCE: 18
tgcccttctt tgccacaatt                                              20

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ttgactagcg gaggctagaa ggaga                                        25

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
aagcggggga gaattagatc gatgg                                        25

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
aaattaaaac atatagtatg ggcaa                                        25

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
agcaaccctc tattgtgtgc atcaa                                        25

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
```
accaaggaag ctttagacaa gatag                                               25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
aaaaagcaca gcaagcagca gctga                                               25

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
agagaccatc aatgaggaag ctgca                                               25

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
agaatgtata gccctaccag cattc                                               25

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
ccgagcaagc ttcacaggag gtaaa                                               25

<210> SEQ ID NO 28
<211> LENGTH: 21
<212> TYPE: DNA
<213> ORGANISM: Artificial Sequence
<220> FEATURE:
<223> OTHER INFORMATION: Probe

<400> SEQUENCE: 28
gtcatcattt cttctagtgt a                                                   21

<210> SEQ ID NO 29
<211> LENGTH: 21
<212> TYPE: DNA
<213> ORGANISM: Artificial Sequence
<220> FEATURE:
<223> OTHER INFORMATION: Probe

<400> SEQUENCE: 29
ttgtctacag ccttctgatg t                                                   21

<210> SEQ ID NO 30
<211> LENGTH: 28
<212> TYPE: DNA
<213> ORGANISM: T7 phage

-continued

```
<220> FEATURE:
<221> NAME/KEY: promoter
<223> OTHER INFORMATION: Promoter sequence for T7 polymerase

<400> SEQUENCE: 30
aattctaata cgactcacta tagggaga                                              28
```